United States Patent [19]

Arthur et al.

[11] 4,330,385

[45] May 18, 1982

[54] DISSOLVED OXYGEN MEASUREMENT INSTRUMENT

[75] Inventors: Robert M. Arthur; Jerome J. Triatik; Robert M. Guell; John F. Masters, all of Fond du Lac, Wis.

[73] Assignee: Arthur Technology, Inc., Fond du Lac, Wis.

[21] Appl. No.: 262,185

[22] Filed: May 11, 1981

Related U.S. Application Data

[63] Continuation of Ser. No. 157,524, Jun. 9, 1980, abandoned.

[51] Int. Cl.³ .......................................... G01N 27/46
[52] U.S. Cl. .................................. 204/195 R; 73/23; 204/1 T
[58] Field of Search .................. 204/1 Y, 1 P, 195 R; 73/23

[56] References Cited

U.S. PATENT DOCUMENTS

3,740,320  6/1973  Arthur .......................... 195/103.5 R
3,810,738  5/1974  Fleischmann ...................... 23/230 R
3,857,761  12/1974  Cummings .......................... 204/1 T
4,018,660  4/1977  Hansen et al. ................... 204/195 R

FOREIGN PATENT DOCUMENTS

818732  8/1959  United Kingdom ............ 204/195 R

OTHER PUBLICATIONS

"Electrochemical Dissolved Oxygen Recorder", Cambridge Instrument Co., Ltd., Preliminary List 323/1, (1957).

Primary Examiner—G. L. Kaplan
Attorney, Agent, or Firm—Quarles & Brady

[57] ABSTRACT

An instrument for measuring the amount of dissolved oxygen in liquids such as waste water includes an enclosure which is partially submerged. Liquid from the main body is continuously circulated through the enclosure and an entrapped volume of air is continuously circulated through the enclosure. The amount of oxygen in this entrapped air is continuously measured by an oxygen concentration sensor which is disposed in the path of the circulating air. This provides an indirect measurement of the amount of dissolved oxygen in the liquid without actually bringing the sensor into contact with the liquid.

3 Claims, 1 Drawing Figure

DISSOLVED OXYGEN MEASUREMENT INSTRUMENT

This is a continuation of application Ser. No. 157,524 filed June 9, 1980 and now abandoned.

BACKGROUND OF THE INVENTION

The field of the invention is the biological treatment of wastewater, and particularly, instruments for measuring the amount of dissolved oxygen in the wastewater being treated.

The concentration of oxygen dissolved in wastewater is an important parameter in industrial and municipal treatment plants. Microorganisms are used to metabolize organic matter found in the wastewater and oxygen is required by the microorganisms to carry out this aerobic metabolic process. Insufficient oxygen either kills the microorganisms or creates a septic, anaerobic condition.

To control the amount of dissolved oxygen in wastewater accurate sensing instruments must be provided. A number of probes for measuring the amount of dissolved oxygen in a liquid are known and are commercially available. In all cases, however, the probes are submerged in the liquid and the dissolved molecular oxygen is reduced at a negatively charged electrode to generate an electric current directly proportional to the oxygen content. To measure dissolved oxygen in wastewater, therefore, the organic contaminants must be separated from the sensing element to enable the electrolytic process to proceed. This is accomplished by employing a selectively permeable membrane which allows the liquid to enter the electrolytic sensing cell when the probe is submerged, but which prevents the passage of contaminants.

Such prior dissolved oxygen measurement instruments have not operated successfully in wastewater with a heavy concentration of solids. The permeable membrane clogs repeatedly and is often torn by solids thus creating a serious maintenance problem.

SUMMARY OF THE INVENTION

The present invention is an instrument for measuring the amount of oxygen dissolved in a liquid, and is particularly useful in measuring the amount of dissolved oxygen in highly contaminated liquids such as wastewater. More particularly, the instrument includes means for entrapping a volume of air in contact with a sample of the liquid, means for continuously exchanging the sample liquid with liquid from the main body, means for circulating the entrapped air through the liquid sample such that the partial pressure of the oxygen in the entrapped air is proportional to the amount of dissolved oxygen in the liquid, and means for measuring the partial pressure of the oxygen in the entrapped air to provide an indication of the amount of oxygen dissolved in the liquid.

A general object of the invention is to provide an instrument in which the sensor is isolated from contaminents in the liquid and which requires little maintenance. This is accomplished by measuring the oxygen content of the entrapped air volume rather than submerging the sensor in the liquid as has been done in the past. The accuracy of the measurement is obtained by continuously circulating the sample liquid with the main body of liquid. In addition, the response of the instrument to changes in oxygen content is enhanced by continuously circulating the entrapped air volume through the sample liquid.

Another object of the invention is to provide a reliable instrument for measuring dissolved oxygen in situ. The instrument may be lowered into the liquid body to insure that the circulated sample is at the same temperature as the main body. In addition, circulation of the liquid sample is achieved without the need for pumps and the associated plumbing otherwise required to remove samples from the liquid body for measurement.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
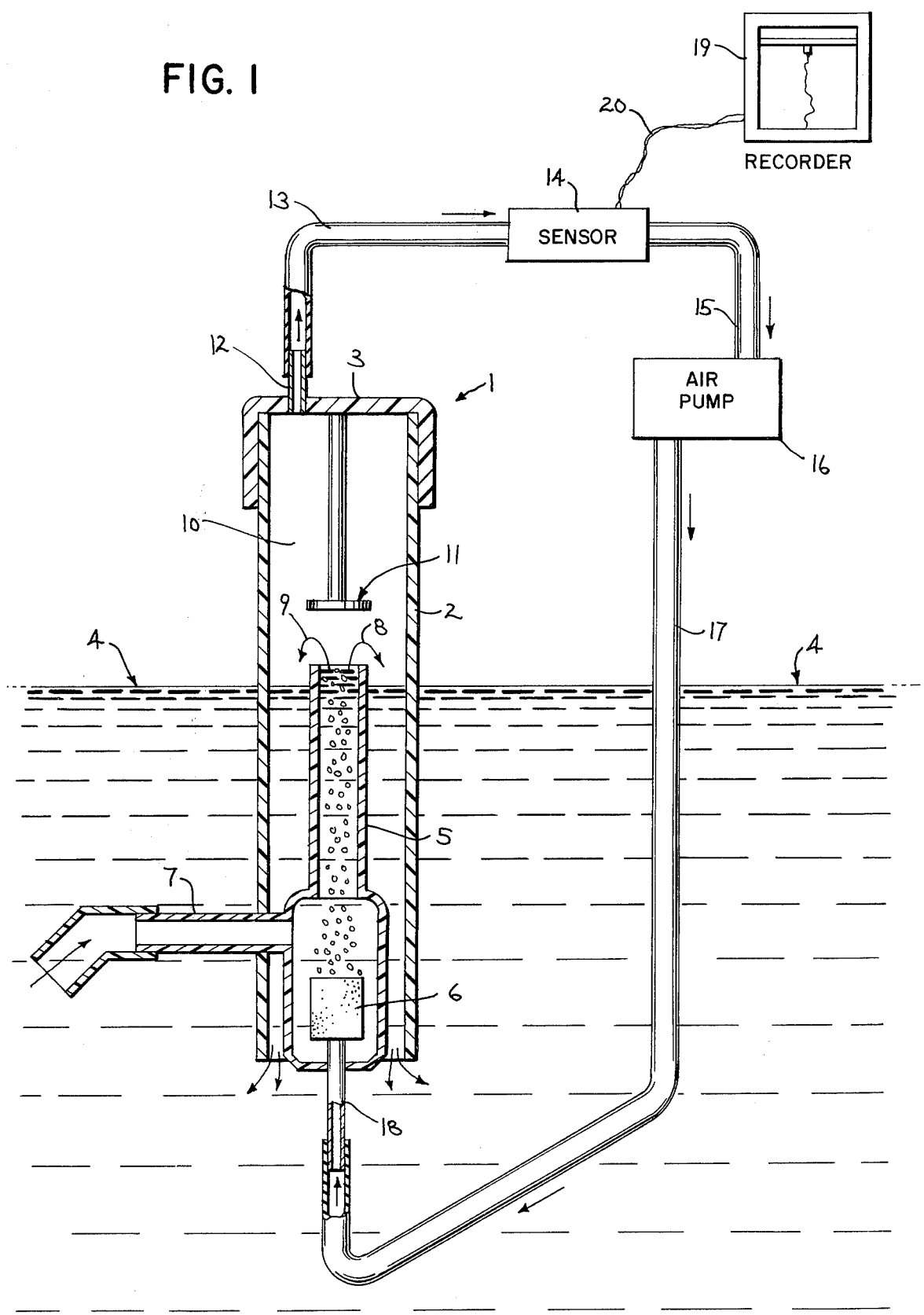
FIG. 1 is a pictorial view of the dissolved oxygen measurement instrument of the present invention.

The dissolved oxygen measurment instrument includes an enclosure 1 formed by a circular cylindrical side wall 2 and a top 3. The enclosure 1 is partially submerged in a body of liquid 4 and its bottom is open to allow a sample of liquid to seek its own level within the enclosure 1. The liquid body 4 may be any body of liquid in which the amount of dissolved oxygen is to be measured and it may include solids and other contaminants which are undergoing treatment.

The liquid sample within the enclosure 1 is continuously circulated with the main body 4 to insure it is at the same temperature and that it contains the same amount of dissolved oxygen. This is accomplished by mounting a chimney 5 within the enclosure 1 and circulating air from a diffuser 6 mounted at the bottom of the chimney 5. A liquid intake pipe 7 connects to the chimney 5 and extends laterally outward therefrom through the side wall 2 of the enclosure 1. The liquid intake pipe 7 communicates with the liquid body 4 and the upward flow of air through the chimney 5 from the diffuser 6 creates a "draft" which continuously draws liquid into the intake pipe 7. The liquid flows up the chimney 5 becoming mixed with the air emanating from the diffuser 6 and it flows over the top rim of the chimney 5 as indicated by arrows 8 and 9. The liquid then flows downward through the annular cavity formed between the chimney 5 and the enclosure side wall 2 and out the open bottom back to the main liquid body 4. This flow of sample liquid is continuous to insure that it accurately reflects the properties of the main liquid body 4, and the flow may be enhanced by positioning the enclosure 1 to take advantage of any currents within the main body of liquid 4.

The enclosure 1 also forms part of an air circulation loop which entraps a volume of air and continuously circulates this air through the sample liquid. A portion of the enclosure 1 extends above the level of the liquid body 4 to form an air cavity 10 within the enclosure 1 above the chimney 5. A splash guard 11 extends downward from the top 3 to a position immediately above the rim of the chimney 5 and an air outlet 12 is formed in the top 3 alongside the splash guard 11. A flexible tube 13 connects the air outlet to an oxygen concentration sensor 14 and the sensor 14 is in turn connected through a tube 15 to the input of an air pump 16. The output of the air pump 16 is connected to a flexible tube 17 which extends downward to connect with an air inlet pipe 18 that extends through the bottom of the chimney 5 and supports the air diffuser 6. An enclosed volume of air is thus defined and is circulated around the resulting loop by the air pump 16 to bring it in intimate contact with both the liquid sample and the oxygen concentration sensor 14.

The oxygen concentration sensor 14 is a commercially available voltametric sensor such as No. TAI P/N B-18970 and TAI P/N B-17828 manufactured by Teledyne Analytical Instruments. It measures the amount of oxygen in the air flowing through the sensor 14 by reducing molecular oxygen at a cathode and generating an electric current which is proportional to the amount. A chart recorder 19 is connected through wires 20 to the sensor 14 and it provides a graphic record of the amount of measured oxygen.

The dissolved oxygen measurement instrument of the present invention measures the amount of dissolved oxygen in the liquid body 4 by measuring the amount of oxygen in the entrapped volume of air. This of course, enables the sensor 14 to be physically separated from the liquid, and more importantly, from the contaminants in the liquid. By continuously circulating entrapped air through the liquid sample, the amount of oxygen in the air becomes proportional to the amount of oxygen in the liquid sample. This oxygen is delivered to the sensor 14 where it is consumed to provide the electrical signal needed to drive the chart recorder 19. Although a relatively small amount of oxygen is consumed in this manner, the oxygen content of the liquid sample is nevertheless reduced by the measurement and would rapidly fall below the oxygen content of the surrounding body of liquid 4. Therefore, to practice the present invention it is imperative that the liquid sample through which the entrapped air is circulated be continuously exchanged with liquid from the main body 4. This insures that the measured oxygen concentration is directly proportional to the amount of dissolved oxygen in the main body of liquid.

The response time of the instrument to changes in dissolved oxygen concentration in the liquid is a function primarily of the speed at which the oxygen concentration in the entrapped air changes to the same level. This response is considerably enhanced by diffusing the air through the liquid sample to bring it into more intimate contact with the dissolved oxygen. This is accomplished in the preferred embodiment by the chimney 5 and air diffuser 6 which provide an instrument that quickly responds to changes in dissolved oxygen concentration. However, other structures are possible, and although they may have slower response times, they may be useful in applications where the rate of change of dissolved oxygen is very low.

It should be apparent that the measurement instrument of the present invention is designed for in situ measurement of dissolved oxygen. This is in sharp contrast to laboratory instruments which analyze a sample of liquid that has been removed from the main body. In situ measurement of dissolved oxygen content according to the present invention provides a continuous flow of oxygen concentration data which enables a chart to be generated without the need for interpolation between sample times. Also, this feature enables the instrument to be used as part of a system for controlling the amount of dissolved oxygen, as for example, in a wastewater treatment plant. The electrical signal generated by the sensor 14 may be input to such a control system as a dissolved oxygen feedback signal and combined with other signals to operate aeration pumps or the like.

We claim:

1. An instrument for measuring the amount of oxygen in a body of liquid, which comprises:
   an enclosure disposed over the body of liquid to entrap a volume of air, the enclosure including:
   (a) an enclosed side wall which is partially submerged in the body of liquid,
   (b) a bottom which has an opening which enables sample liquid to partially fill the enclosure,
   (c) a top wall which entraps air inside the enclosure,
   (d) an intake pipe mounted to the enclosure and providing a liquid passage through the side wall, and
   (e) a chimney mounted inside the enclosure and connected to the intake pipe to direct liquid therefrom upward into contact with the entrapped air, and
   in which said entrapped volume of air is circulated by an air pump connected to the enclosure with a first tube which communicates with the entrapped air inside the enclosure and with a second tube which communicates with the interior of said chimney and an oxygen concentration sensor mounted for contact with said entrapped volume of air to measure the amount of oxygen therein and to thereby indirectly measure the amount of dissolved oxygen in the body of liquid.

2. The instrument as recited in claim 1 in which said second tube extends through a bottom wall on the chimney and is terminated by an air diffuser.

3. An instrument for the in situ measurement of dissolved oxygen in a body of liquid which comprises:
   an enclosure which is submersible in the body of liquid to entrap a volume of air therein and which includes means for continuously circulating sample liquid from the surrounding liquid body into contact with the entrapped volume of air, said means for continuously circulating sample liquid including a chimney disposed in said enclosure and having an intake pipe which receives liquid from the surrounding body of liquid and directs it up the chimney to the liquid surface in contact with the entrapped volume of air;
   a first tube connected to the enclosure to communicate with said entrapped volume of air;
   an oxygen concentration sensor coupled to said first tube and being operable to measure the amount of oxygen in the air circulating in the tube and to thereby provide a continuous, indirect measurement of the amount of dissolved oxygen in the body of liquid,
   a second tube coupled to the oxygen concentration sensor and to the chimney in the enclosure to form a closed loop through which entrapped air is continuously circulated and directed up the chimney to thereby mix with the liquid therein, and
   an air pump which is connected to one of the tubes to circulate the entrapped volume of air around the closed loop.

* * * * *